(12) United States Patent
Misra (10) Patent No.: US 9,873,711 B2
(45) Date of Patent: Jan. 23, 2018

(54) MULTIMERIC DUAL-MODALITY BREAST CANCER DIAGNOSTIC AGENTS (71) Applicant: Preeti Misra, St Louis, MO (US)

(72) Inventor: Preeti Misra, St Louis, MO (US)

( * ) Notice: Subject to any disclaimer, the term of this patent is extended or adjusted under 35 U.S.C. 154(b) by 0 days.

(21) Appl. No.: 14/975,854

(22) Filed: Dec. 21, 2015

(65) Prior Publication Data

US 2016/0168178 A1    Jun. 16, 2016

Related U.S. Application Data (62) Division of application No. 13/610,265, filed on Sep. 11, 2012, now Pat. No. 9,255,116.

(51) Int. Cl.
| | |
|---|---|
| *C07F 9/6524* | (2006.01) |
| *C07F 9/6558* | (2006.01) |
| *A61K 49/00* | (2006.01) |
| *A61K 49/10* | (2006.01) |
| *C07F 9/572* | (2006.01) |
| *A61K 47/54* | (2017.01) |

(52) U.S. Cl.
CPC .......... *C07F 9/6524* (2013.01); *A61K 47/547* (2017.08); *A61K 49/0021* (2013.01); *A61K 49/10* (2013.01); *A61K 49/108* (2013.01); *C07F 9/5728* (2013.01); *C07F 9/6558* (2013.01)

(58) Field of Classification Search
None
See application file for complete search history.

(56) References Cited

PUBLICATIONS

Periodic Table, 2006.*
"Disodium Phosphonate", http://www.chemspider.com/chemical-structure.10653045.html, accessed May 14, 2017.*
"Bisphosphonates", 2002.*

* cited by examiner

*Primary Examiner* — Noble E Jarrell (57) ABSTRACT

The present invention describes dual-modality probes. In particular, the present invention discloses hydroxyapatite specific multimeric bisphosphonate dual-modality MRI and optical probes.

12 Claims, 7 Drawing Sheets

MULTIMERIC DUAL-MODALITY BREAST CANCER DIAGNOSTIC AGENTS

FIELD OF THE INVENTION

The present invention discloses hydroxyapatite specific multimeric bisphosphonate dual-modality MRI and optical probes.

BACKGROUND

Tissue calcification is an important biomarker for human disease, with microcalcifications being of paramount importance for the detection of breast cancer. Microcalcifications ale of two major types. Type I crystals, found more frequently in benign ductal cysts, are birefringent and colorless, and are composed of calcium oxalate {Morgan, 2005}. Type II crystals, most often seen in proliferative lesions and associated with breast cancer cells, are composed of calcium hydroxyapatite, and are non-birefringent and basophilic {Haka, 2002}.

In the general population, breast cancer screening employs x-ray mammography {Van Ongeval, 2006}. In 30% to 50% of cases, microcalcification is the hallmark for the presence of cancer {Morgan, 2003}, although x-ray mammography cannot distinguish the chemical form of the calcium salts present, and therefore relics on the pattern of crystal deposition {Stomper, 2003}.

Mammography is currently the gold standard for the early detection of breast cancer {Bassett, 1992; Bassett 2000}. However, mammography suffers from relatively low sensitivity and specificity {Mavroforou, 2006}, and mammographic screening is limited in certain patient populations {Huo, 2002} and breast densities {Kolb, 2002}. These limitations have spurred interest in alternate modalities to detect breast cancer.

SUMMARY

Imaging methods such as magnetic resonance and optical that could noninvasively and repeatedly measure integrin expression, would be useful in characterizing tumors and in monitoring responses to therapeutic agents. In general, optical imaging methods have high sensitivity and are cost effective at the cell/tissue level. However, most optical imaging apparatus lacks the capacity of tomographic image reconstruction, and therefore 3-dimensional localization of signals in intact tissues/organs has rarely been achieved noninvasively {Li, 2004}. Magnetic resonance imaging (MRI) offers the advantages of being noninvasive, tomographic, and high resolution. However, MRI contrast dependent on endogenous differences in water content and on relaxation time in the tissue of interest. The specificity and sensitivity of MRI is enhanced by contrast agents based on paramagnetic metals such as gadolinium {Bottrill, 2006}.

The co-registration of different molecular imaging modalities provides complementary information. Thus development of multifunctional probes for concurrent imaging applications has become an attractive area. Combining the excellent 3D spatial resolution and unlimited depth penetration of MRI with very high sensitivity of near infrared (NIR) optical imaging should serve to traverse shortcomings of each technology {Massoud, 2003}. NIR tomography has shown the ability to localize changes in functional tissue parameters in vivo, and MRI has the advantage of offering anatomical information about the layered adipose and glandular tissue structure of the breast.

Magnetic resonance and NIR optical concurrent imaging of breast cancer microcalcification has been elusive. Bisphosphonates bind avidly to hydroxyapatite bone mineral surfaces {van Beek, 1998} and have both diagnostic {Ogawa, 2005; Lam, 2007} and therapeutic uses {Lipton, 2000}. Bisphosphonates are analogues of endogenous pyrophosphates in which the hydrolysable oxygen atom that separates the two phosphate groups is replaced with a more stable carbon atom. The P—C—P structure is responsible for giving bisphosphonates their high affinity for bone, which can be further enhanced by addition of a hydroxyl group at the central carbon atom {van Beek, 1998}. An ideal molecular imaging targeting ligand for magnetic resonance and NIR optical concurrent detection of hydroxyapatite microcalcification of breast cancer is 1-hydroxy-1, 1-bisphosphonate derivatives {Bhushan, 2008; Bhushan, 2007}, which shows remarkable specificity for hydroxyapatite, which is common in malignant breast disease, over other calcium salts, such as calcium oxalate, which is typically deposited in benign lesions and is rarely seen in malignancies {Morgan, 2005; Baker, 2007}.

Nature often takes advantage of multimerization to decrease ligand off-rate and improve affinity of cell surface binders {Kitov, 2003; Mammen, 1998}. There is a general need to find suitable scaffolds for the assembly of multiple targeting ligands and contrast agents in hope that multimerization would improve the performance of cancer specific ligands.

Several different multivalent scaffolds have been used successfully in past particularly for applications in carbohydrate/lectin interactions {Lindhorst, 2002; Lundquist, 2002} but also for peptide/protein interactions {Wright, 2001} and in context of tumor targeting {Carlson, 2007; Thumshirn, 2003}. Among these scaffolds are small molecules with few conjugation sites (~2-10) and larger systems like dendrimers {Voegtle, 2007} and polymers {Haag, 2006}.

The present invention describes a development of multimeric hydroxyapatite specific dual-modality MRI and optical probes. A system to combine high sensitivity of NIR optical imaging in a planar tomographic geometry with 3D spatial resolution and unlimited depth penetration of MRI for breast imaging is described. In particular, the present invention describes a chemical system for the efficient production of a tri-functional agent comprised of a NIR fluomphore for optical imaging, a metal chelate for simultaneous MRI, and a bisphosphonate specific for hydroxyapatite, the major calcium salt produced during osteoblastosis. The multimeric hydroxyapatite specific dual-modality MRI and optical probes could theoretically bind multivalently and thus more avidly to target hydroxyapatite. Multifunctional probes for concurrent imaging applications could traverse shortcomings of each technology and could provide complementary information.

In one aspect of present invention, an organic chelating ligand is reacted with a trifunctional linker moiety, having primary amine and carboxylic acid functional groups, followed by conjugation with a bisphosphonate to result in a bisphosphonate conjugated organic chelating ligand. Deprotection of one or more functional groups on a bisphosphonate conjugated organic chelating ligand yields one or more free functional groups. Chelation of a metal ion on one or more free functional groups results in a metal chelate. Conjugation of a NIR fluorophore on a metal chelate results in a dual-modality MRI and optical probe (FIG. 1) In such aspect, trifunctional linker moiety 2 is amino acid, polymer, or dendrimer. $L_1$, $L_2$, and $L_3$ are independently selected from alkane, polyethylene glycol, and polypropylene glycol.

Metal ion, M is independently selected from Cu, Fc, In, Tm, Yb, Y, Gd, Eu, and a lanthanide. R is t-butyl ester, ester, or hydrogen. $R^1$ is Boc, Fmoc, Ac, Cbz, Bz, and Bn. In one embodiment, amino acid is natural amino acid. In some embodiment, amino acid is unnatural amino acid. In some embodiments, alkane is C0-C20 straight chain carbon unit. In some embodiments, polyethylene glycol is 1 to 20 ethylene glycol unit. In some embodiments, polypropylene glycol is 1 to 20 propylene glycol unit. In some embodiments, bisphosphonate, BP is independently selected from alendronate, etidronate, ibandronate, incadronate, neridronate, olpadronate, pamidronate, risedronate, tiludronate, and zoledronate. In some embodiments, IRDye is a NIR fluorophore independently selected from the group of IRDye 78, IRDye 700DX, VivoTag-S 750, VivoTag 800, VivoTag-S 680, DY-750, DY-682, DY-675, Cypate, Cy7, Alexa Fluor 750, and Alexa Fluor 680.

In an another aspect of present invention, a bisphosphonate is conjugated with multivalent scaffold followed by deprotection of amino protecting group to generate an amine containing bisphosphonate conjugated multivalent scaffold. Reaction of an amine containing bisphosphonate conjugated multivalent scaffold with a trifunctional linker moiety conjugated organic chelating ligand 3 (FIG. 1) results in an organic chelating ligand containing bisphosphonate conjugated multivalent scaffold 9 (FIG. 2). Deprotection of one or more functional groups on an organic chelating ligand containing bisphosphonate conjugated multivalent scaffold, followed by a metal chelation and conjugation with a NIR fluorophore yields a multimeric dual-modality MRI and optical probe. In such aspect, $R^1$ is independently selected from Boc, Fmoc, Ac, Cbz, Bz, and Bn. R is t-butyl ester, ester, or hydrogen. $R^2$, $R^3$, and $R^4$ are bisphosphonates or OH. Metal ion, M is independently selected from Cu, Fe, In, Tm, Yb, Y, Gd, Eu, and a lanthanide. $L_1$, $L_2$, $L_3$, $L_4$, and $L_5$ are linkers independently selected from alkane, amino acid, —NHCO(CH$_2$)$_5$—, polyethylene glycol, and polypropylene glycol. In one embodiment, amino acid is natural amino acid. In some embodiments, amino acid is unnatural amino acid. In some embodiments, an alkane is C0-C20 straight chain carbon unit. In some embodiments, polyethylene glycol is 1 to 20 ethylene glycol unit. In some embodiments, polypropylene glycol is 1 to 20 propylene glycol unit. In some embodiments, bisphosphonate is independently selected from alendronate, etidronate, ibandronate, incadronate, neridronate, olpadronate, pamidronate, risedronate, tiludronate, and zoledronate. In some embodiments, IRDye is a NIR fluorophore independently selected from the group of IRDye 78, IRDye 700DX, VivoTag-S 750, VivoTag 800, VivoTag-S 680, DY-750, DY-682, DY-675, Cypate, Cy7, Alexa Fluor 750, and Alexa Fluor 680.

The present invention describes dual-modality probes. Particularly, the present invention discloses hydroxyapatite specific multimeric bisphosphonate dual-modality MRI and optical probes. Dual-modality probes of present invention provide complementary information. The major medical application of present invention is in the high sensitivity simultaneous NIR optical and MRI detection of tissue calcification, especially microcalcification in breast cancer, without the need for ionizing radiation.

DETAILED DESCRIPTION

In a present invention, synthetic strategy is developed for multimeric bisphosphonate dual-modality probes for targeted imaging of breast cancer microcalcification. Particularly, present invention describes a chemical system for the efficient production of a tri-functional agent comprised of a NIR fluorophore for optical imaging, a metal chelate for simultaneous MRI, and a bisphosphonate specific for hydroxyapatite, the major calcium salt produced during osteoblastosis. Dual-modality probes of present invention allows cross validation and direct comparison between MRI and NIR optical imaging.

The multimeric bisphosphonate dual-modality probes of present invention are prepared according to the methods known in the art, as illustrated in FIGS. 1-4 and described for specific compounds in examples 1-3. Products are characterized by analytical HPLC, NMR, and LC-MS. Monomeric dual-modality probes are obtained in typical yields of 55-65% and trimeric dual-modality probes are obtained in typical yields of 20-30%.

Figure 1:
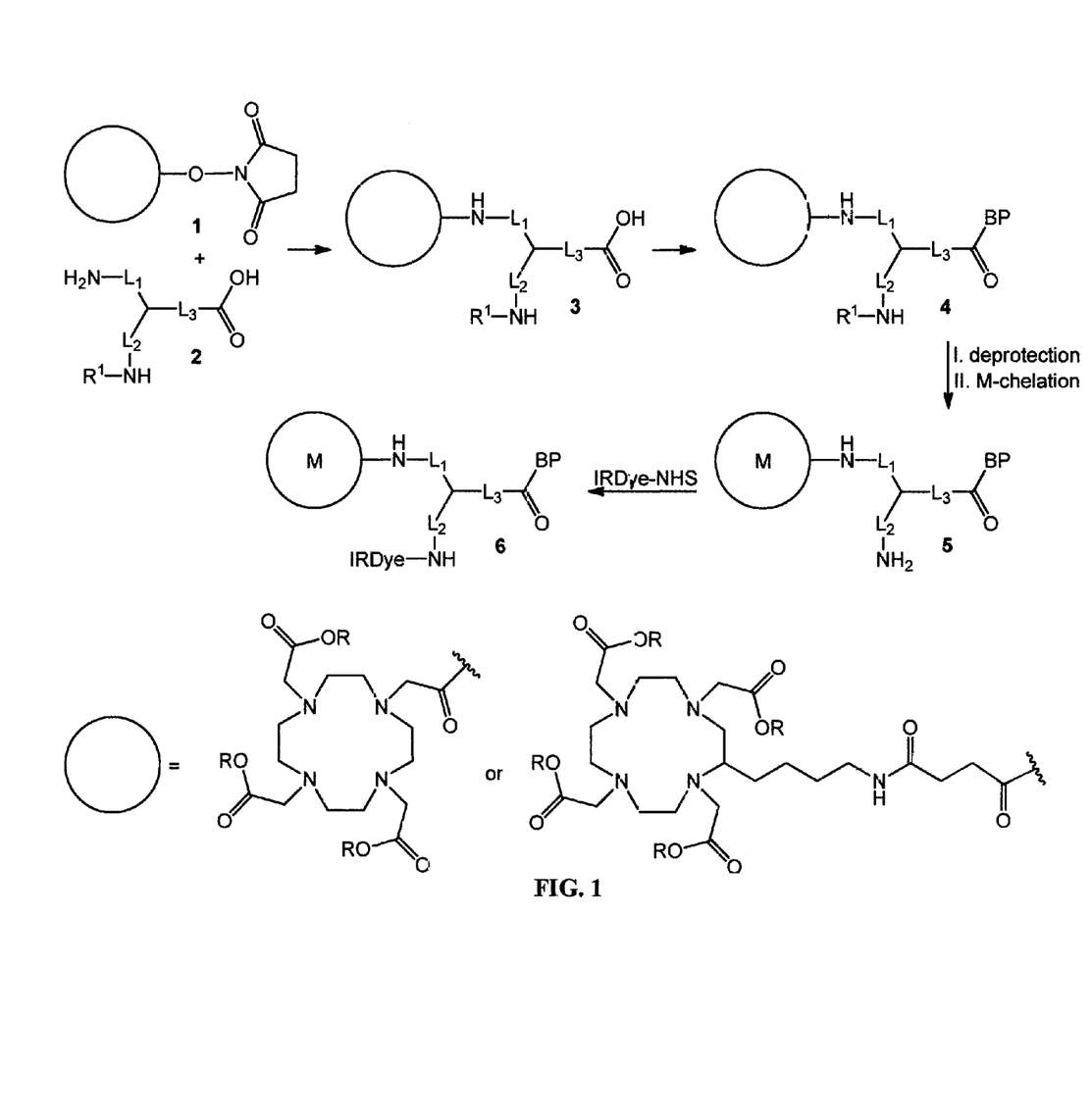
FIG. 1 represents a dual-modality probe in which a NIR fluorophore is conjugated after a metal ion chelation.
Figure 2:
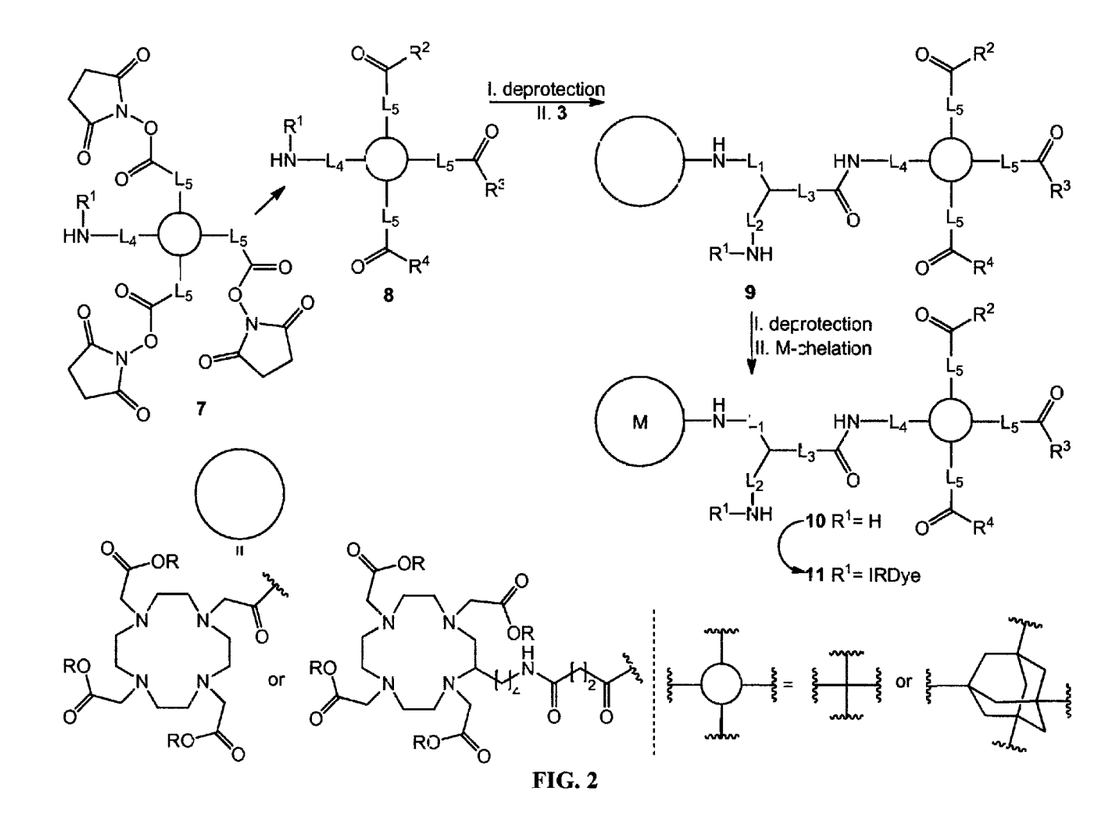
FIG. 2 represents a multimeric dual-modality probe in which a NIR fluorophore is conjugated after a metal ion chelation.

FIG. 1 of present invention describes a synthetic scheme for a dual-modality probe in which a NIR fluorophore is conjugated after a metal ion chelation. An organic chelating ligand is reacted with a trifunctional linker moiety, followed by conjugation with a bisphosphonate to result in a bisphosphonate conjugated organic chelating ligand. Deprotection of one or more functional groups on a bisphosphonate conjugated organic chelating ligand yields one or more free functional groups. Chelation of a metal ion on one or more free functional groups results in a metal chelate, followed by conjugation of a NIR fluorophore to result in a dual-modality MRI and optical probe.

FIG. 2 of present invention describes a synthetic scheme for a multimeric dual-modality probe in which a NIR fluorophore is conjugated after a metal ion chelation. A bisphosphonate is conjugated with a multivalent scaffold, followed by deprotection of an amino protecting group to generate an amine containing bisphosphonate conjugated multivalent scaffold. Reaction of an amine containing bisphosphonate conjugated multivalent scaffold with a trifunctional linker moiety conjugated organic chelating ligand 3 (FIG. 1) results in an organic chelating ligand containing bisphosphonate conjugated multivalent scaffold 9. Deprotection of one or more functional groups on an organic chelating ligand containing bisphosphonate conjugated multivalent scaffold, followed by a metal chelation and conju- gation with a NIR fluorophore yields a multimeric dual-modality MRI and optical probe.

Figure 3:
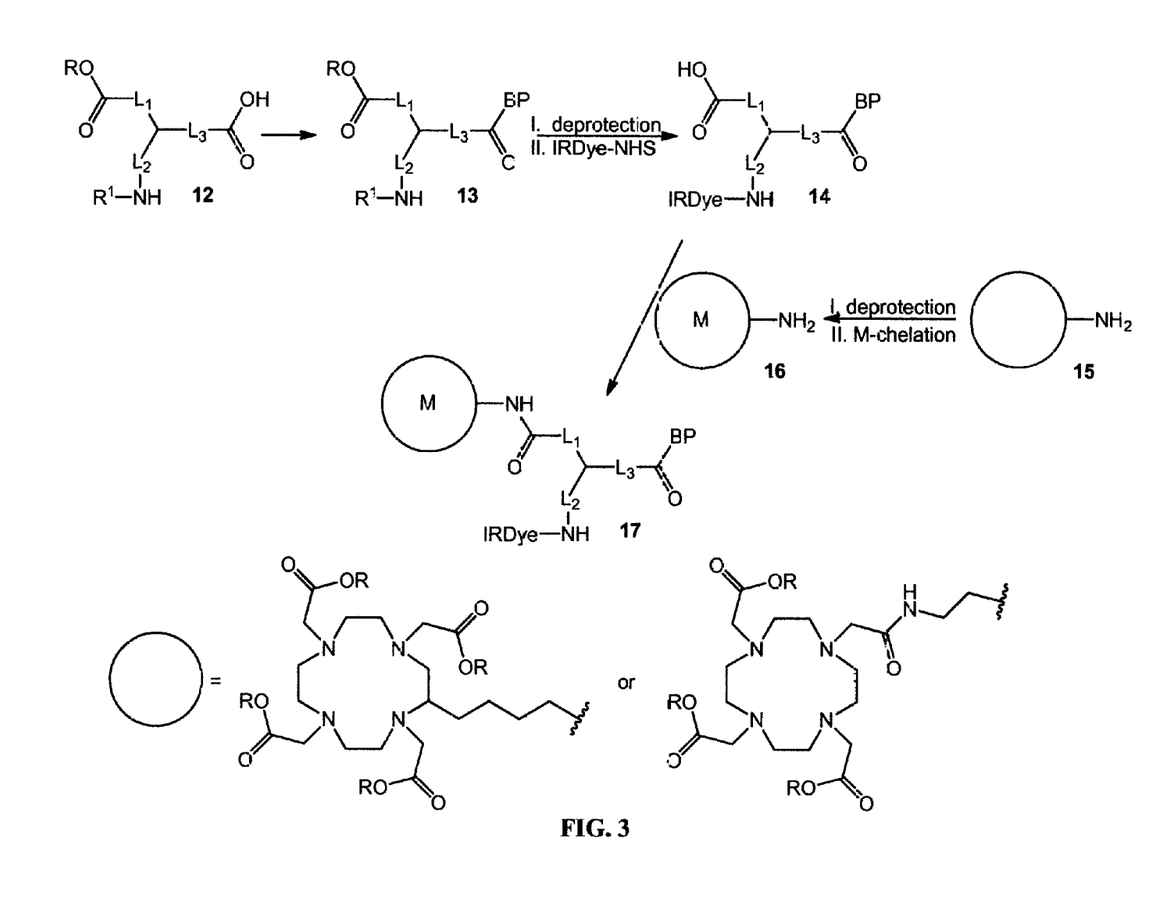
FIG. 3 represents a dual-modality probe in which a NIR fluorophore is conjugated before a reaction with a metal chelate.

FIG. 3 of present invention describes a synthetic scheme for a dual-modality probe in which a NIR fluorophore is conjugated before a reaction with a metal chelate. A bisphosphonate is conjugated with a trifunctional linker moiety, followed by deprotection and conjugation with a NIR fluorophore to result in a NIR fluorophore containing bisphosphonate conjugated carboxylic acid precursor 14. Reaction of a metal chelate 16 with a NIR fluorophore containing bisphosphonate conjugated carboxylic acid precursor 14 results in a dual modality probe 17.

Figure 4:
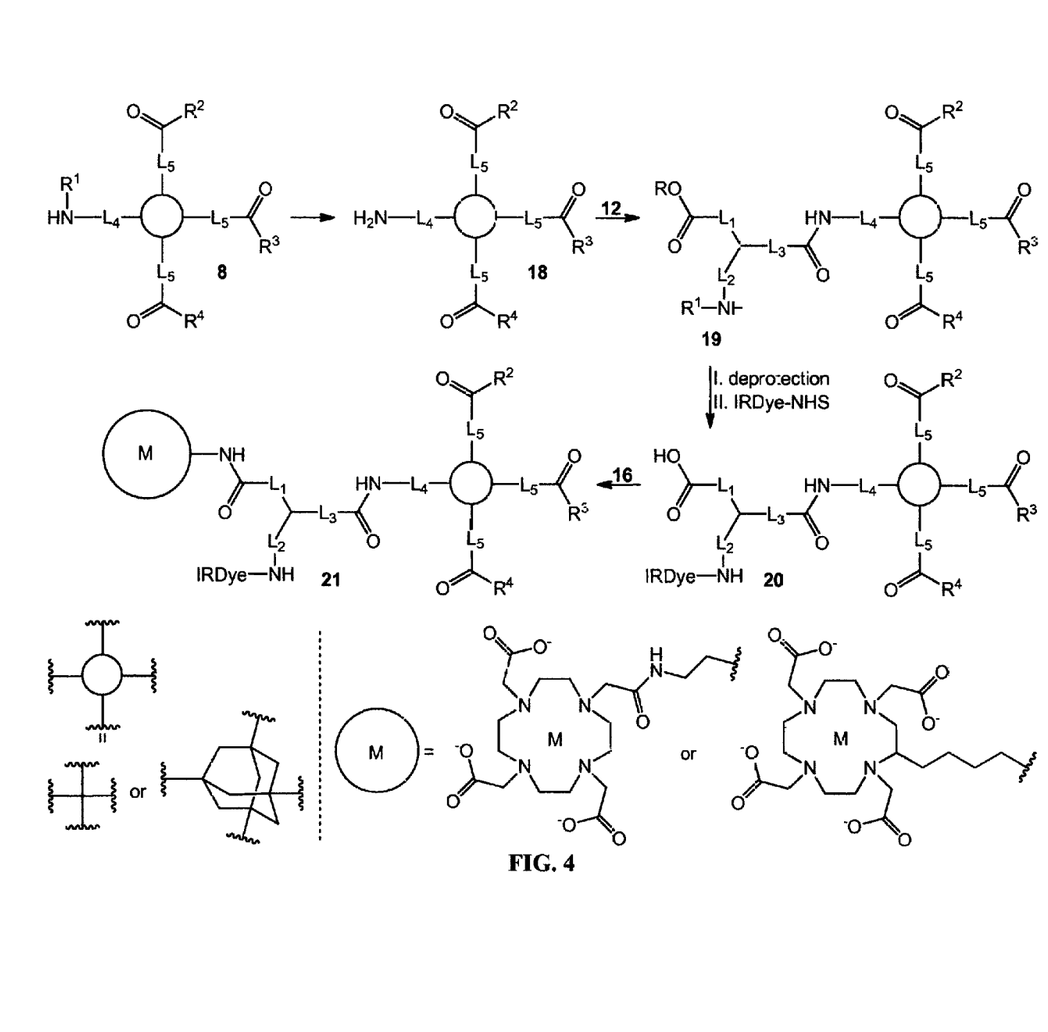
FIG. 4 represents a multimeric dual-modality probe in which a NIR fluorophore is conjugated before a reaction with a metal chelate.

FIG. 4 of present invention describes a synthetic scheme for a multimeric dual-modality probe in which a NIR fluorophore is conjugated before a reaction with a metal chelate. A bisphosphonate is conjugated with a multivalent scaffold followed by deprotection of an amino protecting group to generate an amine containing bisphosphonate conjugated multivalent scaffold. Reaction of an amine containing bisphosphonate conjugated multivalent scaffold with a trifunctional linker moiety, followed by deprotection and NIR fluorophore conjugation results in a NIR fluorophore containing bisphosphonate conjugated multivalent scaffold 20. Reaction of a metal chelate 16 with a NIR fluorophore containing bisphosphonate conjugated multivalent scaffold 20 results in a multimeric dual-modality probe 21.

In one aspect, the present invention provides a dual-modality probe having a formula selected from the group of:

In such aspect,

BP is a bisphosphonate,

$L_1$, $L_2$, $L_3$, $L_4$, and $L_5$ are linkers,

IRDye is a near infrared dye with wavelength in the range of 700-900 nm, and is a metal chelate independently selected from:

, and

In one embodiment, linkers are independently selected from alkane, amino acid, —NHCO(CH$_2$)$_5$—, polyethylene glycol, and polypropylene glycol. In some embodiments, amino acid is natural amino acid. In some embodiments, amino acid is unnatural amino acid. In some embodiments, alkane is C0-C20 straight chain carbon unit. In some embodiments, polyethylene glycol is 1 to 20 ethylene glycol unit. In some embodiments, polypropylene glycol is 1 to 20 propylene glycol unit. In some embodiments, M is independently selected from Cu, Fe, In, Tm, Yb, Y, Gd, Eu, and a lanthanide. In some embodiments, near infrared dye is independently selected from the group of IRDye 78, IRDye 700DX, VivoTag-S 750, VivoTag 800, VivoTag-S 680, DY-750, DY-682, DY-675, Cypate, Cy7, Alexa Fluor 750, and Alexa Fluor 680. In some embodiments, bisphosphonate is independently selected from the group of alendronate, etidronate, ibandronate, incadronate, neridronate, olpadronate, phosphonate, pamidronate, risedronate, tiludronate, and zoledronate.

In an another aspect, the present invention provides a method of making a dual-modality probe. The method involves steps of:

(a) Starting synthesis with an organic chelating ligand selected from the group of:

, and where, R is t-butyl ester, ester, or hydrogen, and $R^1$ is (b) reacting a organic chelating ligand with a trifunctional linker moiety to result in a trifunctional linker moiety conjugated organic chelating ligand, (c) reacting a trifunctional linker moiety conjugated organic chelating ligand with a bisphosphonate to result in a bisphosphonate conjugated organic chelating ligand, (d) deprotecting one or more functional groups on a bisphosphonate conjugated organic chelating ligand to yield one or more free functional groups, (e) chelating a metal ion on one or more free functional groups to result in a metal chelate, and (f) conjugating a NIR fluorophore with a metal chelate to result in a dual-modality probe.

In one embodiment, bisphosphonate is selected from the group of:

where, $L_1$, and $L_2$ are independently selected from alkane, amino acid, —NHCO(CH$_2$)$_5$—, polyethylene glycol, and polypropylene glycol, and $R^2$, $R^3$, and $R^4$ are independently selected from alendronate, etidronate, ibandronate, incadronate, neridronate, olpadronate, pamidronate, risedronate, tiludronate, zoledronate, and OH. In some embodiments, trifunctional linker moiety is selected from amino acid, polymer, and dendrimer. In some embodiments, amino acid is natural amino acid. In some embodiments, amino acid is unnatural amino acid. In some embodiments, alkane is C0-C20 straight chain carbon unit. In some embodiments, polyethylene glycol is 1 to 20 ethylene glycol unit. In some embodiments, polypropylene glycol is 1 to 20 propylene glycol unit. In some embodiments, metal ion is independently selected from Cu, Fe, In, Tm, Yb, Y, Gd, Eu, and a lanthanide. In some embodiments, NIR fluorophore is independently selected from the group of IRDye 78, IRDye 800CW, IRDye 700DX, VivoTag-S 750, VivoTag 800, VivoTag-S 680, DY-750, DY-682, DY-675, Cypate, Cy7, Alexa Fluor 750, and Alexa Fluor 680. In some embodiments, bisphosphonate is independently selected from the group of alendronate, etidronate, ibandronate, incadronate, neridronate, olpadronate, phosphonate, pamidronate, risedronate, tiludronate, and zoledronate.

In an another aspect, the present invention provides a method of making a dual-modality probe. The method involves steps of:

(a) Starting a synthesis with reacting a bisphosphonate with a trifunctional linker moiety to result in a trifunctional linker moiety conjugated bisphosphonate, (b) deprotecting one or more functional groups on a trifunctional linker moiety conjugated bisphosphonate to yield me or more free functional groups, (c) conjugating a NIR fluorophore to result in a NIR fluorophore containing trifunctional linker moiety conjugated bisphosphonate carboxylic acid precursor, (d) providing a metal chelate selected from the group of:

and (e) reacting a metal chelate with a NIR fluorophore containing trifunctional linker moiety conjugated bisphosphonate carboxylic acid precursor under a condition capable of forming an amide bond to result in a dual-modality probe.

In one embodiment, bisphosphonate is selected from the group of:

where, $L_1$, and $L_2$ are independently selected from alkane, amino acid, —NHCO(CH$_2$)$_5$—, polyethylene glycol, and polypropylene glycol, and $R^2$, $R^3$, and $R^4$ are independently selected from alendronate, etidronate, ibandronate, incadronate, neridronate, olpadronate, pamidronate, risedronate, tiludronate, zoledronate, and OH. In some embodiments, trifunctional linker moiety is selected from amino acid, polymer, and dendrimer. In some embodiments, amino acid is natural amino acid. In some embodiments, amino acid is unnatural amino acid. In some embodiments, alkane is C0-C20 straight chain carbon unit. In some embodiments, polyethylene glycol is 1 to 20 ethylene glycol unit. In some embodiments, polypropylene glycol is 1 to 20 propylene glycol unit. In some embodiments, M is independently selected from Cu, Fe, In, Tm, Yb, Y, Gd, Eu, and a lanthanide. In some embodiments, NIR fluorophore is independently selected from the group of IRDye 78, IRDye 700DX, VivoTag-S 750, VivoTag 800, VivoTag-S 680, DY-750, DY-682, DY-675, Cypate, Cy7, Alexa Fluor 750, and Alexa Fluor 680. In some embodiments, bisphosphonate is independently selected from the group of alendronate, etidronate, ibandronate, incadronate, neridronate, olpadronate, phosphonate, pamidronate, risedronate, tiludronate, and zoledronate.

With high quantum yields, the spectral properties of dual-modality MRI and optical probes demonstrates peak absorptions (770-780 nm) and emission (790-800 nm), located within the "NIR window," an area of the electromagnetic spectrum that maximizes photon penetration and recovery in living tissue.

The multimeric bisphosphonate dual-modality probes generated by present invention can be used for, e.g., optical, magnetic resonance, radioimmuno, PET, and SPECT applications for detection, imaging and treatment of breast cancer microcalcification and other abnormalities. In particular, multimeric bisphosphonate dual-modality MRI and optical probes generated by present invention are hydroxyapatite specific for detection of breast cancer microcalcification. Specifically, trimerization of bisphosphonate using a multivalent scaffold results in significantly higher in vitro specificity for hydroxyapatite, a major mineral component of calcification and normal bone, over other calcium salts, in comparison to monomeric bisphosphonate dual-modality probe without a multivalent scaffold.

To determine the selectivity and specificity of [Gd-DOTA]-Lys-IRDye-Alen monomer and [Gd-DOTA]-Asp-IRDye-Ad-Alen trimer for hydroxyapatite, a major mineral component of calcifications and normal bone, over other calcium salts, in the present invention an incubation of equal quantity each of Ca-hydroxyapatite, Ca-pyrophosphate, Ca-phosphate, Ca-oxalate, and Ca-carbonate salts with [Gd-DOTA]-Lys-IRDye-Alen monomer/[Gd-DOTA]-Asp-IRDye-Ad-Alen trimer in phosphate buffered saline (PBS) is performed. NIR fluorescence images are acquired after incubation and washing of crystals, dual-modality probes has many fold higher specificity for hydroxyapatite over other calcium salts found in the body and permits high sensitivity detection of hydroxyapatite.

EXAMPLES

Figure 5:
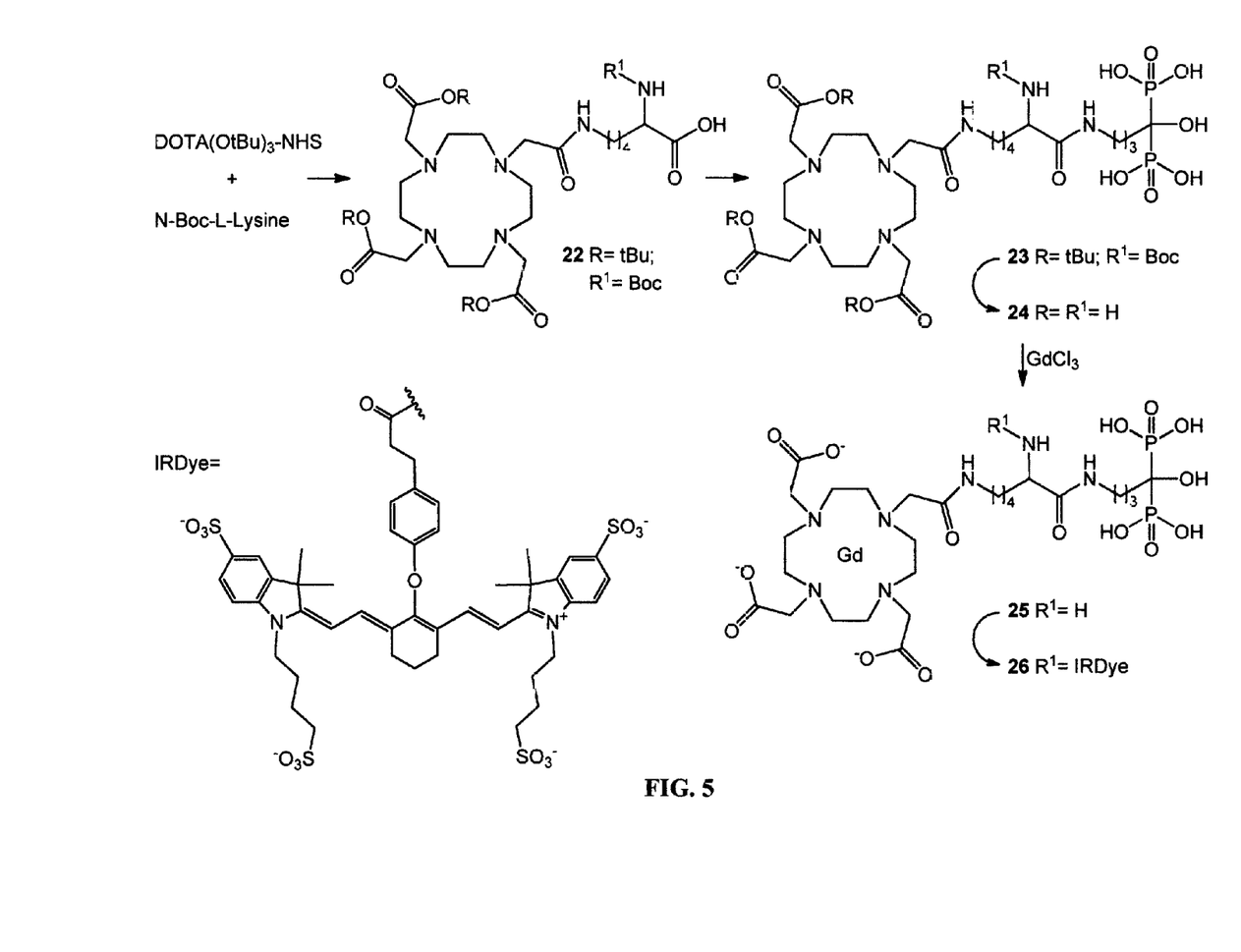
FIG. 5 represents a synthetic scheme for preparation of [Gd-DOTA]-Lys-IRDye-Alen monomer.

1. Preparation of [Gd-DOTA]-Lys-IRDye-Alen Monomer (FIG. 5)

DOTA(OtBu)$_3$-Boc-Lys:

To a solution of Boc-L-Lysine (0.06 mmol) in 0.4 mL DMF at 0° C., is added triethylamine (0.12 mmol) followed by dropwise addition of DOTA(OtBu)$_3$ NHS ester (0.05 mmol) in 0.5 mL DMF for 10 min with stirring. After 10 min, the ice bath is removed and stirring is continued at room temperature (RT) for 6 h. The reaction mixture is poured over 2 mL ice-cold water and purified by preparative HPLC to obtain DOTA(OtBu)$_3$-Boc-Lys 22.

DOTA(tBu)$_3$-Boc-Lys-Alen:

Alendronic acid (0.05 mmol), HCTU (0.05 mmol), and N-methylmorpholine (NMM; 0.20 mmol) are added at RT under N$_2$ atmosphere to 0.05 mmol DOTA(OBu)$_3$-Boc-Lys 22 in DMSO (1 mL). After stirring for 3 h at RT, the reaction mixture is poured over 3 mL ice-cold water and an intermediate DOTA(tBu)$_3$-Boc-Lys-Alen 23 is purified by preparative HPLC.

DOTA-Lys-Alen:

DOTA(tBu)$_3$-Boc-Lys-Alen 23 (0.045 mmol) is taken in 95% trifluoroacetic acid (TFA, 1 mL). The solution is stirred at RT for 6 h then removed the acid by N$_2$ stream. After lyophilization, DOTA-Lys-Alen 24 is obtained without further purification as a white powder.

[Gd-DOTA]-Lys-Alen:

The chelation of Gd$^{3+}$ is performed by adding 50 μL of 1 M GdCl$_3$ in water to a solution of DOTA-Lys-Alen 24 (0.04 mmol) in 950 μL of 0.5 M HAc/Ac$^-$ buffer, pH 5.5. The reaction mixture is stirred at RT for 12 h. The compound is purified by preparative HPLC to obtain [Gd-DOTA]-Lys-Alen 25.

[Gd-DOTA]-Lys-IRDye-Alen monomer:

To [Gd-DOTA]-Lys-Alen 25 (0.01 mmol) in 1 mL DMSO, is added NHS ester of the NIR fluorophore IRDye 78 (IRDye-NHS, 0.01 mmol) and N,N-diisopropylethylamine (0.05 mmol) at 0° C. under nitrogen atmosphere. The stirring is continued for 2 h at RT in the dark. The reaction mixture is poured over 4 mL ice-cold water, purified by HPLC and concentrated on an Oasis HLB desalting cartridge as described previously (Bhushan, 2008). On lyophilization a bright green solid reaction component, [Gd-DOTA]-Lys-IRDye-Alen monomer 26 is obtained.

Figure 6:
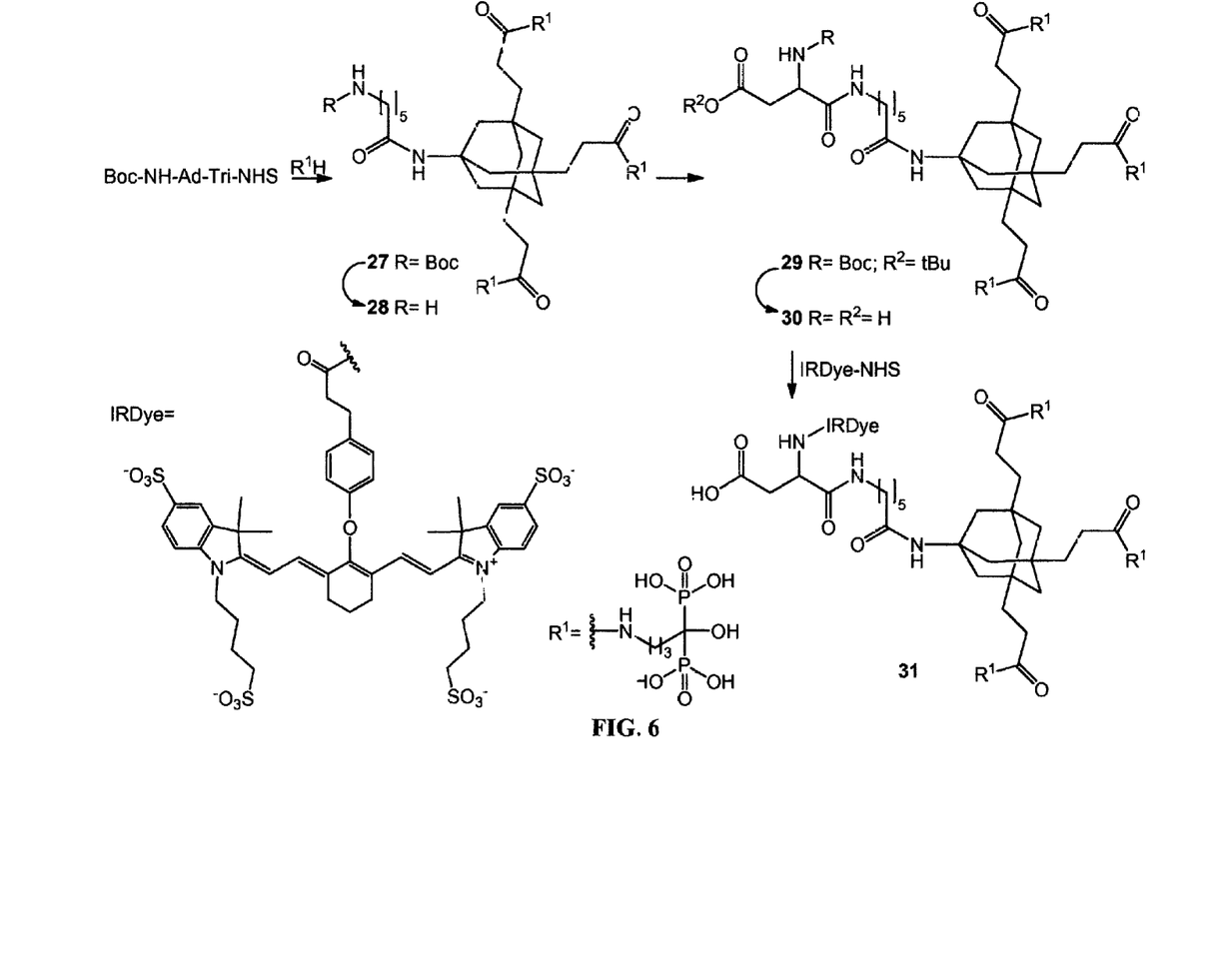
FIG. 6 represents a synthetic scheme for preparation of Asp-IRDye-Ad-Alen trimer.

2. Preparation of Asp-IRDye-Ad-Alen Trimer (FIG. 6)

Ad-Alen Trimer:

Alendronic acid (0.06 mmol) is dissolved in 1 mL of DMSO and triethylamine (0.30 mmol). After 5 min, a solution of Boc-NH-Ad-Tri-NHS (0.015 mmol) {Humblet, 2009} in 0.2 mL of DMSO is added. The reaction mixture is stirred at RT for 16 h. The compound 27 is purified after dilution into a final volume of 5 mL with ice-cold water by preparative HPLC system. After lyophilization, product 27 is treated with 95% TFA (1 mL) for 3 h. Excess TFA is removed under nitrogen and after lyophilization the Ad-Alen trimer 28 is obtained.

Asp-Ad-Alen Trimer:

To Ad-Alen trimer 28 (0.01 mmol) in 0.5 mL DMF at 0° C., is added triethylamine (0.15 mmol) followed by dropwise addition of Boc-L-Asp(OtBu)—OSu (0.01 mmol) in 0.4 mL DMF for 10 min with stirring. After 10 min, the ice bath is removed and stirring is continued at RT for 6 h. The reaction mixture is poured over 2 mL ice-cold water and purified by preparative HPLC to obtain compound 29. After lyophilization, compound 29 is treated with 95% TFA (1 mL) for 6 h. Excess TFA is removed under nitrogen and after lyophilization the Asp-Ad-Alen timer 30 is obtained.

Asp-IRDye-Ad-Alen Trimer:

To Asp-Ad-Alen trimer 30 (0.01 mmol) in 1 mL DMSO, is added NHS ester of the NIR fluorophore IRDye 78 (IRDye-NHS, 0.01 mmol) and N,N-diisopropylethylamine (0.15 mmol) at 0° C. under nitrogen atmosphere. The stirring is continued for 2 h at RT in the dark. The reaction mixture is poured over 4 mL ice-cold water, purified by HPLC and concentrated on an Oasis HLB desalting cartridge as described previously {Bhushan, 2008}. On lyophilization a bright green solid reaction component, Asp-IRDye-Ad-Alen trimer 31 is obtained.

Figure 7:
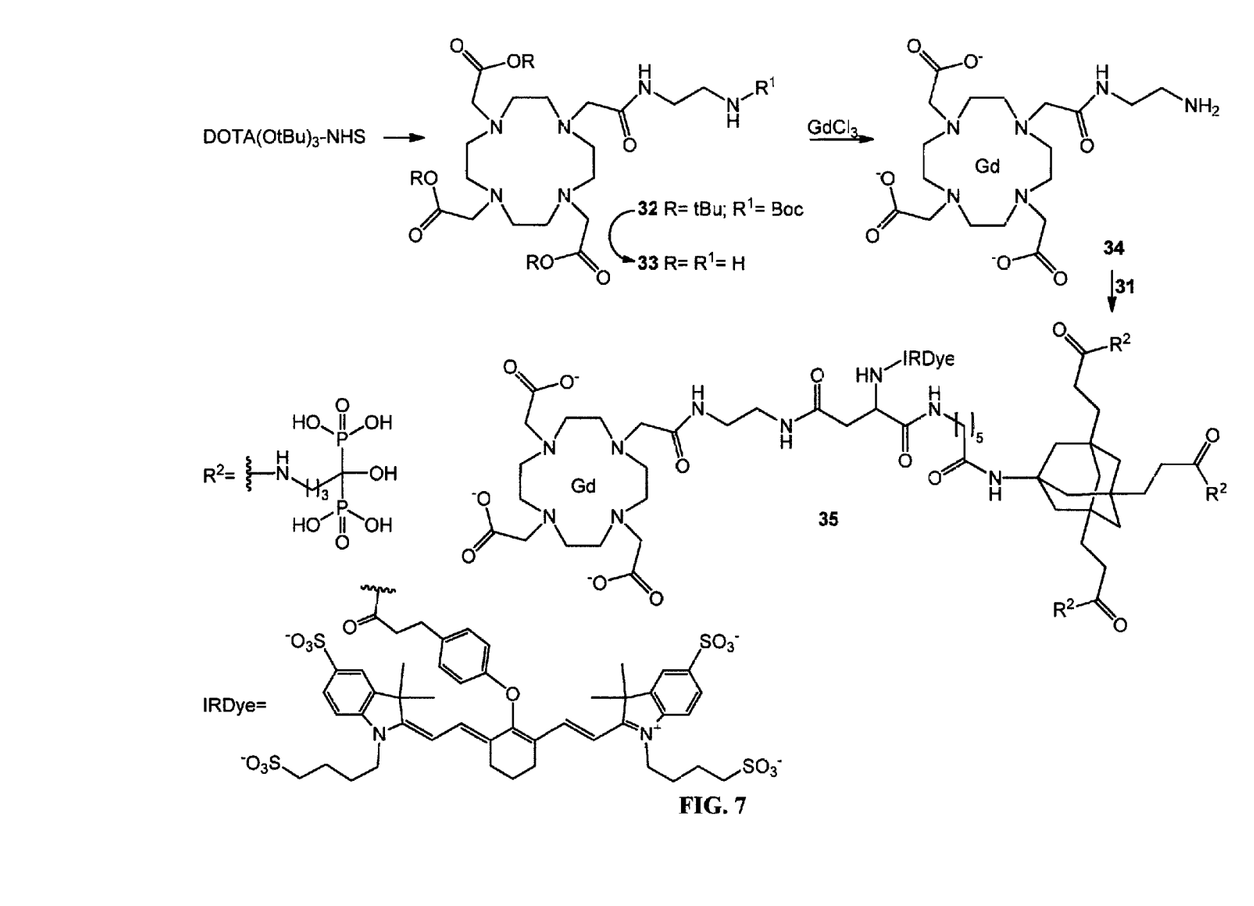
FIG. 7 represents a synthetic scheme for preparation of [Gd-DOTA]-Asp-IRDye-Ad-Alen trimer.

3. Preparation of [Gd-DOTA]-Asp-IRDye-Ad-Alen Trimer (FIG. 7)

DOTA(OtBu)$_3$-Boc-Diaminoethane:

To a solution of Roc-1,2-diaminoethane (0.06 mmol) in 0.4 mL DMF at 0° C., is added triethylamine (0.12 mmol) followed by dropwise addition of DOTA(OtBu)$_3$ NHS ester (0.05 mmol) in 0.5 mL DMF for 10 min with stirring. After 10 min, the ice bath is removed and stirring is continued at RT for 6 h. The reaction mixture is poured over 2 mL ice-cold water and purified by preparative HPLC to obtain DOTA(OtBu)$_3$-Boc-diaminoethane 32

DOTA-Diaminoethane:

DOTA(OtBu)$_3$-Boc-diaminoethane 32 (0.045 mmol) is taken in 95% TFA (1 mL). The solution is stirred at RT for 6 h then removed the acid by N$_2$ stream. After lyophilization, DOTA-diaminoethane 33 is obtained without further purification as a white powder,

[Gd-DOTA]-diaminoethane:

The chelation of Gd$^{3+}$ is performed by adding 50 μL of 1 M GdCl$_3$ in water to a solution of DOTA-diaminoethane 33 (0.04 mmol) in 950 μL of 0.5 M HAc/Ac$^-$ buffer, pH 5.5. The reaction mixture is stirred at RT for 12 h. The compound is purified by preparative HPLC to obtain [Gd-DOTA]-diaminoethane 34.

[Gd-DOTA]-Asp-IRDye-Ad-Alen Trimer:

To a solution of Asp-IRDye-Ad-Alen trimer 31 (0.01 mmol) in 1 mL DMSO at 0° C., is added HCTU (0.01 mmol) and NMM (0.15 mmol) followed by dropwise addition of [Gd-DOTA]-diaminoethane 34 (0.01 mmol) in 0.5 mL DMF for 10 min with stirring. After 10 min, the ice bath is removed and stirring is continued at RT for 2 h in the dark. The reaction mixture is poured over 2 mL ice-cold water and purified by preparative HPLC to obtain [Gd-DOTA]-Asp-IRDye-Ad-Alen trimer 35.

4. In Vitro Calcium Salt Specificity Experiments 5 mg/mL of hydroxyapatite or the phosphate, oxalate, carbonate, and pyrophosphate salts of calcium are separately incubated with 100 nM [Gd-DOTA]-Asp-IRDye-Ad-Alen trimer in 100 mL PBS for 30 min with continuous vortexing at RT. Crystals are washed 4 times with a 100-fold excess of PBS, centrifuged and visualized using the NIR fluorescence imaging system {Bhushan, 2008) at a fluence rate of 5 mW/cm$^2$. All NIR fluorescence images have identical exposure times and normalizations. Similarly, calcium salt binding study is performed with Gd-DOTA]-Lys-IRDye-Alen monomer in a same condition.

REFERENCES

1. Morgan M P, Cooke M M, McCarthy G M. Microcalcifications associated with breast cancer: an epiphenomenon or biologically significant feature of selected tumors. *J. Mammary Gland Biol. Neoplasia* 2005, 10, 181-187.
2. Haka A S, Shafer-Peltier K E, Fitzmaurice M, Crowe J, Dasari R R, Feld M S. Identifying microcalcifications in benign and malignant breast lesions by probing differences in their chemical composition using Raman spectroscopy. *Cancer Res.* 2002, 62, 5375-5380.
3. Van Ongeval C, Bosmans I I, Van Steen A. Current status of digital mammography for screening and diagnosis of breast cancer. *Curr. Opin. Oncol.* 2006, 18, 547-554.
4. Stomper P C, Geradts J, Edge S B, Levine E G. Mammographic predictors of the presence and size of invasive carcinomas associated with malignant microcalcification lesions without a mass. *AJR Am. J. Roentgenol.* 2003, 181, 1679-1684.
5. Bassett L W. Mammographic analysts of calcifications. *Radiol. Clin. North Am.* 1992, 30, 93-105.
6. Bassett L W. Digital and computer-aided mammography. *Breast J.* 2000, 6, 291-293.
7. Mavroforou A, Mavrophoros D, Michalodimitrakis E. Screening mammography, public perceptions, and medical liability. *Eur. J. Radiol.* 2006, 57, 428-435.
8. Huo Z, Giger M L, Olopade O I, et. al. Computerized analysis of digitized mammograms of BRCA1 and BRCA2 gene mutation carriers. *Radiology* 2002, 225, 519-526.
9. Kolb M, Lichy J, Newhouse J H. Comparison of the performance of screening mammography, physical examination, and breast U S and evaluation of factors that influence them: an analysis of 27,825 patient evaluations. *Radiology* 2002, 225, 165-175.
10. Li H, Gray B D, Corbin I, et. al. M R and fluorescence imaging of low-density lipoprotein receptors. *Acad. Radiol.* 2004, 11, 1251-1259.
11. Bottrill M, Kwok L, Long N J. Lanthanides in magnetic resonance imaging. *Chem. Soc. Rev.* 2006, 35, 557-571.
12. Massoud T F, Gambhir S S. Molecular imaging in living subjects: seeing fundamental biological processes in a new light. *Genes Dev.* 2003, 17, 545-580.
13. Van Beek E R, Lowik C W, Ebetino F H, Papapoulos S E. Binding and antiresorptive properties of heterocycle-containing bisphosphonate analogs: structure-activity relationships. *Bone* 1998, 23, 431-442.
14. Ogawa K, Mukai T, Arano Y, et. al. Development of a rhenium-186-labeled MAG3-conjugated bisphosphonate for the palliation of metastatic bone pain based on the concept of bifunctional radiopharmaceuticals. *Bioconjug. Chem.* 2005, 16, 751-757.
15. Lam M G E H, de Klerk J M H, van Rijk P P, Zonnenberg B A. Bone seeking radiopharmaceuticals for palliation of pain in cancer patients with osseous metastases. *Anti-cancer Agents in Med. Chem.* 2007, 7, 381-397.
16. Lipton A, Theriault R L, Hortobagyi, G N, et. al. Pamidronate prevents skeletal complications and is effective palliative treatment in women with breast carcinoma and osteolytic bone metastases: long term follow-up of two randomized, placebo-controlled trials. *Cancer* 2000, 88, 1082-1090.
17. Bhushan K R, Misra P, Liu F, et. al. Detection of breast cancer microcalcifications using a dual-modality SPECT/NIR fluorescent probe. *J. Am. Chem. Soc.* 2008, 130, 17648-17649.
18. Bhushan K R, Tanaka E. Franbioni J V. Synthesis of conjugatable bisphosphonates for molecular imaging of large animals. *Angew. Chem. Int. Ed. Engl.* 2007, 46, 7969-7971.
19. Baker R, Matousek P, Ronayne K L, Parker A W, Rogers K, Stone N. Depth profiling of calcifications in breast tissue using picosecond Kerr-gated Raman spectroscopy. *Analyst* 2007, 132, 48-53.
20. Kitov P I, Bundle D R. On the nature of the multivalency effect: a thermodynamic model. *J. Am. Chem. Soc.* 2003, 125, 16271-16284.

21. Mammen M, Chio S K, Whitesides G M. Polyvalent interactions in biological systems: implications for design and use of multivalent ligands and inhibitors. *Angew. Chem., Int. Ed.* 1998, 37, 2755-2794, 22. Lindhorst T K. Artificial multivalent sugar ligands to understand and manipulate carbohydrate-protein interactions. *Top. Curr. Chem.* 2002, 218, 201-235.

23. Lundquist J J, Toone E J. The cluster glycoside effect. *Chem. Rev.* 2002, 102, 555-578.

24. Wright D, Usher L. Multivalent binding in the design of bioactive compounds. *Curr. Org. Chem.* 2001, 5.1107-1131

25. Carlson C, Mowery P, Owen R, Dykhuizen E, Kiessling, L. Selective tumor cell targeting using low-affinity, multivalent interactions. *ACS Chem. Biol.* 2007, 2, 119-127.

26. Thumshirn G, Hersel U, Goodman S L, Kessler H. Multimeric cyclic RGD peptides as potential tools for tumor targeting: solid-phase peptide synthesis and chemoselective oxime ligation. *Chem. Eur J.* 2003, 9, 2717-2725.

27. Voegtle F, Richardt G, Werner N. *Dendritische Molekule*; B. G. Teubner Verlag: Wiesbaden, Germany, 2007.

28. Haag R, Kratz F. Polymer therapeutics: concepts and applications. *Angew. Chem. Int. Ed.* 2006, 45, 1198-1215.

29. Humblet V, Misra P, Bhushan K R, et al. Multivalent scaffolds for affinity maturation of small molecule cell surface binders and their application to prostate tumor targeting. *J. Med. Chem.* 2009, 52, 544-550.

What is claimed is:

1. A method of making a dual-modality probe, said method comprising:
   (a) providing an organic chelating ligand, wherein said organic chelating ligand selected from the group of:

, and wherein

R is t-butyl ester, ester, or hydrogen; and $R^1$ is (b) reacting said organic chelating ligand with a trifunctional linker moiety to result in a trifunctional linker moiety conjugated organic chelating ligand;

(c) reacting said trifunctional linker moiety conjugated organic chelating ligand with a bisphosphonate to result in a bisphosphonate conjugated organic chelating ligand;

(d) deprotecting one or more functional groups on said bisphosphonate conjugated organic chelating ligand to yield one or more free functional groups;

(e) chelating a metal ion on said one or more free functional groups to result in a metal chelate; and (f) conjugating a near infrared fluorophore with said metal chelate to result in said dual-modality probe, wherein said near infrared fluorophore is selected from the group consisting of IRDye 78, IRDye 700DX, VivoTag-S 750, VivoTag 800, VivoTag-S 680, DY-750, DY-682, DY-675, Cypate, Cy7, Alexa Fluor 750, and Alexa Fluor 680.

2. The method of claim 1, wherein said trifunctional linker moiety is amino acid, polymer, or dendrimer.

3. The method of claim 1, wherein said metal ion is selected from the group consisting of Cu, Fe, In, Mn, Tm, Yb, Y, Gd and Eu.

4. The method of claim 1, wherein said metal ion and said near infrared fluorophore are conjugated for concurrent magnetic resonance and near infrared optical imaging.

5. The method of claim 1, wherein said bisphosphonate is selected from the group consisting of alendronate, incadronate, neridronate, olpadronate, pamidronate, risedronate, and zoledronate.

6. The method of claim 1, wherein said bisphosphonate is selected from the group consisting of:

17

-continued wherein
L$_1$, and L$_2$ are independently selected from alkane, amino acid, —NHCO(CH$_2$)$_5$—, polyethylene glycol, and polypropylene glycol; and
R$^2$, R$^3$, and R$^4$ are independently selected from alendronate, incadronate, neridronate, olpadronate, phosphonate, pamidronate, risedronate, and zoledronate.

7. A method of making a dual-modality probe, said method comprising:
(a) reacting a bisphosphonate with a trifunctional linker moiety to result in a trifunctional linker moiety conjugated bisphosphonate, wherein said bisphosphonate and said trifunctional linker moiety are connected by amide bonds;
(b) deprotecting one or more functional groups on said trifunctional linker moiety conjugated bisphosphonate to yield one or more free functional groups;
(c) conjugating a near infrared fluorophore to result in a near infrared containing trifunctional linker moiety conjugated bisphosphonate carboxylic acid precursor, wherein said near infrared fluorophore and said trifunctional linker moiety are connected by amide bonds, wherein said near infrared fluorophore is selected from the group consisting of IRDye 78, IRDye 700DX, VivoTag-S 750, VivoTag 800, VivoTag-S 680, DY-750, DY-682, DY-675, Cypate, Cy7, Alexa Fluor 750, and Alexa Fluor 68;
(d) providing a metal chelate, wherein said metal chelate selected from the group of:

18 and
(e) reacting said metal chelate with said near infrared containing trifunctional linker moiety conjugated bisphosphonate carboxylic acid precursor under a condition capable of forming an amide bond to result in said dual-modality probe.

8. The method of claim 7, wherein said trifunctional linker moiety is amino acid, polymer, or dendrimer.

9. The method of claim 7, wherein M is selected from the group consisting of Cu, Fe, In, Mn, Tm, Yb, Y, Gd, and Eu.

10. The method of claim 7, wherein said dual-modality probe is in a form of pharmaceutically acceptable salts, hydrates, and solvates.

11. The method of claim 7, wherein said bisphosphonate is selected from the group consisting of alendronate, incadronate, neridronate, olpadronate, pamidronate, risedronate, and zoledronate.

12. The method of claim 7, wherein said bisphosphonate is selected from the group consisting of:

and wherein
L$_1$, and L$_2$ are independently selected from alkane, amino acid, —NHCO(CH$_2$)$_5$—, polyethylene glycol, and polypropylene glycol; and
R$^2$, R$^3$, and R$^4$ are independently selected from alendronate, incadronate, neridronate, olpadronate, phosphonate, pamidronate, risedronate, and zoledronate.

* * * * *